US012741094B2

(12) United States Patent
Lee et al.

(10) Patent No.: US 12,741,094 B2
(45) Date of Patent: Sep. 22, 2026

(54) TECHNIQUES FOR IMPROVED AUTOMATIC DRUG DELIVERY PERFORMANCE USING DELIVERY TENDENCIES FROM PAST DELIVERY HISTORY AND USE PATTERNS

(71) Applicant: INSULET CORPORATION, Acton, MA (US)

(72) Inventors: Joon Bok Lee, Acton, MA (US); Jason O'Connor, Acton, MA (US); Yibin Zheng, Hartland, WI (US)

(73) Assignee: INSULET CORPORATION, Acton, MA (US)

( * ) Notice: Subject to any disclaimer, the term of this patent is extended or adjusted under 35 U.S.C. 154(b) by 154 days.

(21) Appl. No.: 18/499,515

(22) Filed: Nov. 1, 2023

(65) Prior Publication Data

US 2024/0058534 A1 Feb. 22, 2024

Related U.S. Application Data

(62) Division of application No. 17/123,369, filed on Dec. 16, 2020, now Pat. No. 11,833,329.

(Continued)

(51) Int. Cl.
*A61M 5/172* (2006.01)
*A61M 5/142* (2006.01)

(52) U.S. Cl.
CPC ...... *A61M 5/1723* (2013.01); *A61M 5/14244* (2013.01); *A61M 2005/14208* (2013.01);

(Continued)

(58) Field of Classification Search
CPC .......... A61M 2005/14208; A61M 2205/3303; A61M 2205/3569; A61M 2205/502;

(Continued)

(56) References Cited

U.S. PATENT DOCUMENTS 7,837,647 B2 * 11/2010 Estes .................... G16H 20/17 604/65
8,467,980 B2 * 6/2013 Campbell ......... A61M 5/14244 702/50

(Continued)

OTHER PUBLICATIONS

"Understanding Insulin on Board (IOB)", Alberta Diabetes Link (Year: 2016).

*Primary Examiner* — Quynh-Nhu H. Vu
(74) *Attorney, Agent, or Firm* — Goodwin Procter LLP

(57) ABSTRACT

Disclosed are a device, system, methods and computer-readable medium products that provide techniques to implement functionality to receive blood glucose measurements over a period of time. An average of missing blood glucose measurement values may be maintained over a predetermined time period. A count of a number of missing blood glucose measurement values over a period of time may be established. A controller may calculate a divergence of the number of missing blood glucose measurement values over the period of time from the average of missing blood glucose measurements over the predetermined time period. Based on a value of the divergence, a determination that a safety constraint for delivery of insulin is to be reduced. The safety constraint may be reduced by a predetermined percentage. An instruction to deliver an insulin dosage may be generated according to the reduced safety constraint may be forwarded to a wearable drug delivery device.

20 Claims, 7 Drawing Sheets

Related U.S. Application Data

(60) Provisional application No. 62/951,384, filed on Dec. 20, 2019.

(52) U.S. Cl.
CPC ............... *A61M 2205/3303* (2013.01); *A61M 2205/3569* (2013.01); *A61M 2205/502* (2013.01); *A61M 2205/52* (2013.01); *A61M 2230/201* (2013.01)

(58) Field of Classification Search
CPC ........ A61M 2205/52; A61M 2230/201; A61M 5/14244; A61M 5/1723; G16H 20/17; G16H 40/67; G16H 50/20; G16H 50/30
See application file for complete search history.

(56) References Cited

U.S. PATENT DOCUMENTS

| | | | | |
|---|---|---|---|---|
| 9,597,451 | B2 * | 3/2017 | Yodfat | G16H 20/17 |
| 9,798,859 | B2 * | 10/2017 | Yodfat | G05D 7/0676 |
| 10,543,313 | B2 * | 1/2020 | Damiano | A61M 5/1723 |
| 2015/0073337 | A1 | 3/2015 | Saint | |
| 2017/0172473 | A1 | 6/2017 | Wedekind | |
| 2020/0197605 | A1 | 6/2020 | Haidar | |

* cited by examiner

TECHNIQUES FOR IMPROVED AUTOMATIC DRUG DELIVERY PERFORMANCE USING DELIVERY TENDENCIES FROM PAST DELIVERY HISTORY AND USE PATTERNS

CROSS-REFERENCE TO RELATED APPLICATIONS

This application is a division of U.S. application Ser. No. 17/123,369, filed Dec. 16, 2010, which claims the benefit of the filing date of U.S. Provisional Application Ser. No. 62/951,384, filed Dec. 20, 2019, the entire contents of which are incorporated herein by reference in their entirety.

BACKGROUND

Due to the complicated and dynamic nature of the human body's response to insulin, it is unfortunately common for patients to end up in a hypoglycemic or hyperglycemic state after being treated with insulin therapy. This outcome is undesirable for many reasons: hypoglycemia creates an immediate risk of a severe medical event (seizure, coma, death) while hyperglycemia creates long term negative health effects as well as the risk of ketoacidosis. Whether a person ends up in one of these states depends on a combination of data inputs and responses.

Some closed-loop insulin delivery systems operate on specific, hard safety constraints on insulin delivery that define fixed limits on insulin delivery. These hard safety constraints that may be universally applied to all users may unduly limit optimization of insulin delivery specific to each user.

Automatic insulin delivery systems when assessing the user's insulin needs incorporate models of blood glucose and insulin interactions to calculate its recommendations. The models may be too rigid and may also unduly limit the predictive capabilities of the automatic insulin delivery systems when evaluating the blood glucose and insulin interactions of a specific user.

The ability of closed-loop insulin delivery systems to adjust delivery based on user physiology is limited based on input parameters that do not accurately reflect specific user physiology in real time or substantially real time.

In addition to the models and input parameters being limited, some automated insulin delivery systems are limited to reliance on a single data stream (continuous glucose monitor (CGM) estimated glucose value (EGV) readings) to calculate the recommended insulin deliveries. There are other efforts to utilize additional sensors (such as heart rate, skin temperature, skin impedance, accelerometry) to gain more data streams, but these implementations require additional body real estate for the sensors and increased cost of the sensors.

It would be beneficial if techniques and systems were developed to address the above problems as well as others.

DETAILED DESCRIPTION

Figure 1:
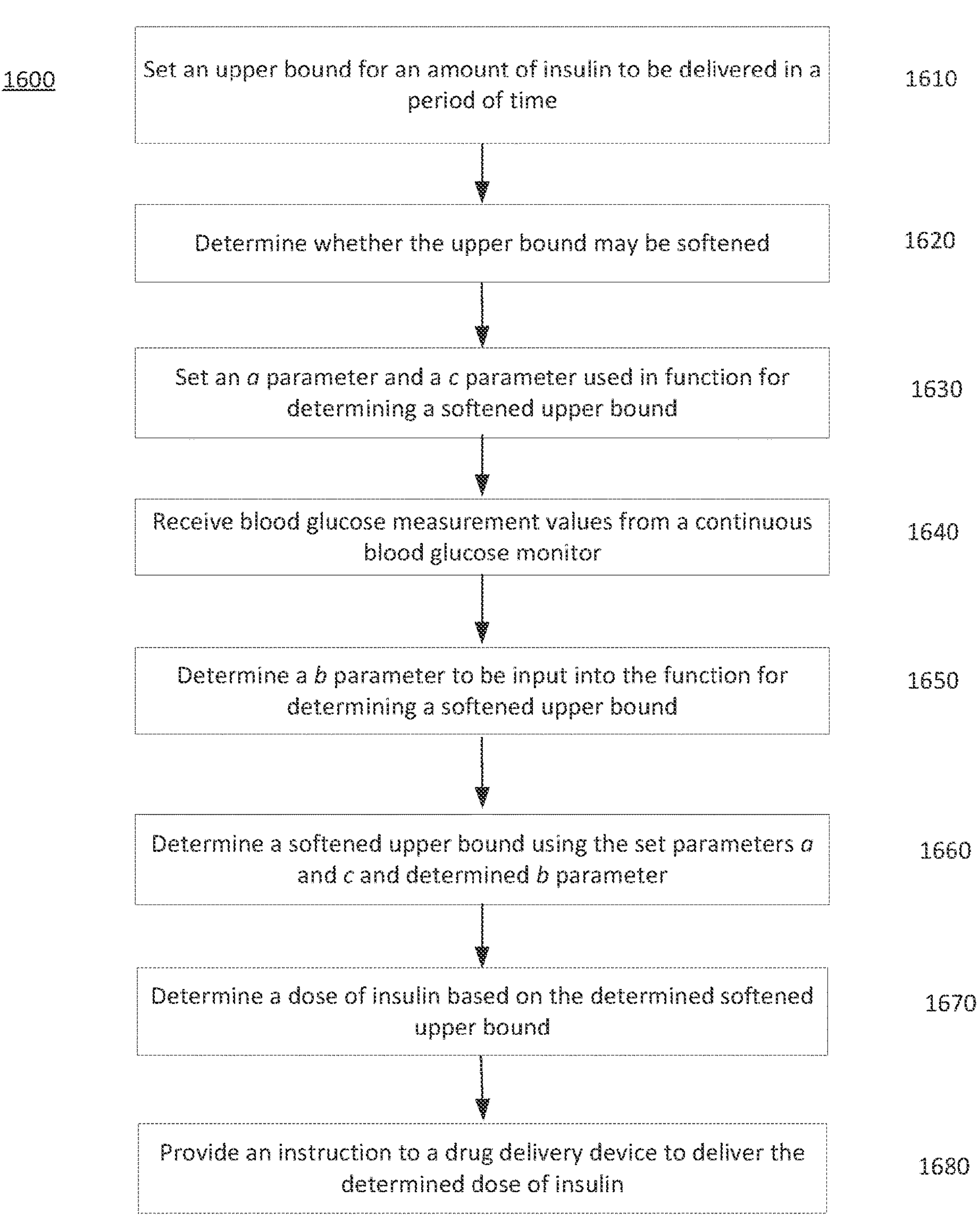
FIG. 1 shows a flow chart of an example of a process for determining a softened upper bound for delivery of insulin.

An example of a dynamic, personalized (control-outcome dependent) real-time softening of hard safety constraints in closed loop artificial pancreas systems generally relates to any closed loop insulin delivery system that operates on specific, hard safety constraints on insulin delivery to improve the closed loop insulin delivery system's robustness against hypoglycemia (i.e., low blood sugar). Closed loop artificial pancreas systems rely on blood glucose measurement values obtained by a continuous blood glucose monitor or the like that are evaluated by a personal diabetes management device to regulate a person's blood glucose. These specific, hard safety constraints are generally defined as fixed limits on insulin delivery at each actuation (e.g., delivery of insulin) and may be dependent on thresholds of blood glucose values or past insulin delivery histories. However, the interaction of blood glucose values and insulin deliveries in actual human bodies are never in stasis or equilibrium, and thus fixed safety constraints that are commonly implemented in these systems may be improved by implementing "soft" asymptotic limits instead, which may be dynamically personalized based on user-inputted clinical parameters, glucose variability, or real-time control outcomes. For instance, instead of incorporating a fixed limit on total insulin delivery for any given cycle (e.g., a measurement of blood glucose and a delivery of a dosage of insulin based on the blood glucose measurement), a parameterized threshold may be incorporated above which the penalization on insulin delivery may be proportionally increased. Both the value of this parametrized threshold as well as the "softness" or "permeability" of this threshold may be customized by a variety of factors individual to each person with type 1 diabetes mellitus (T1DM). This implementation reduces any closed loop insulin delivery system's dependence on ad hoc safety constraints and allows the safety of the system to adapt dynamically to the needs of each user.

In an example, the following describes advanced, on-line updates of glucose prediction models for optimum closed loop artificial pancreas algorithm performance with compatible architectural change generally relates to establishing a model of glucose and insulin interactions in a person with Type 1 Diabetes. The model may be used by an AP application to project what is going to happen with an automatic insulin delivery (AID) system with respect to the model. In an example, the model may be fixed. But in other examples, the model may be adjustable. While there may be efforts that are utilizing artificial intelligence and machine learning processes to provide a real-time adjustable model, these real-time artificial intelligence and machine learning processes require an amount of computational power that exceeds the capabilities of the wearable or portable sensors or device, such as diabetes management devices, continuous glucose monitoring devices, or drug delivery devices.

Closed loop insulin delivery algorithms that automatically assess the user's insulin needs may incorporate these models of glucose and insulin interactions to calculate recommendations for timing and doses of insulin delivery. The following discloses examples of 1) Online updates of model parameters based on residuals between model predictions and actual glucose values, where residuals may be a difference between predictions and actual values; 2) Higher order models (incorporation of insulin deliveries from prior history) of glucose deliveries; 3) Inclusion of advanced insulin effects beyond simple insulin delivery; and 4) Inclusion of glucose rate of changes beyond auto-regressive model of glucose values only.

In an example of a hardware implementation of a real-time model adjustment, the example processes may be implemented on a blood glucose sensor. The blood glucose sensor may, for example, be a continuous blood glucose monitor (CGM) that may be operable to receive insulin delivery information from a personal diabetes management device and CGM, Rate of change (RoC) values (e.g., rate of change of the blood glucose measurements over time) sent as part of the advertising packet in Bluetooth low energy (BLE) available for use by any insulin delivery pump.

The described process and hardware implementations provide improvements in the predictive capabilities of any model of glucose and insulin interactions in people with (Type 1 Diabetes) T1D or (Type 1 Diabetes Mellitus) T1DM and may improve the closed loop control outcomes in any algorithm, not just the AP application examples discussed herein that utilizes these models.

An example describes methods for continuous, personalized adjustment of automated insulin delivery in artificial pancreas systems for T1DM applications relates to adjustment of automated insulin delivery systems for people with type 1 diabetes, and specifically to Artificial Pancreas (AP) systems that execute automatic closed loop insulin delivery by linking a continuous glucose monitor (CGM) with an insulin pump. The algorithm to calculate the amount of insulin delivered based on the input continuous glucose monitor value must be robustly designed and capable of modifying its behavior depending on the user's physiology. This disclosure outlines novel methods for more accurate reflection of the user's changing insulin needs in real time within the closed loop algorithms by, for example, adjusting the input TDI clinical parameter based on mean glucose deviations from the target, and adjusting the gain of any algorithm's model based on actual clinical glucose trajectories.

An example describes methods of identification of improved automated insulin delivery performance through user insulin delivery tendencies from past delivery history and user insulin pump use patterns relates to solving a problem with automated insulin delivery systems that are limited to reliance on a single data stream, such as estimated glucose value (EGV) readings from a continuous glucose monitor (CGM), to calculate recommended insulin deliveries. There are other efforts to utilize additional sensors (such as heart rate, skin temperature, skin impedance, accelerometry, and the like) to gain more data streams, but these implementations require additional body real estate for the sensors and the increased cost of the respective sensors.

In an example, an automatic insulin delivery (AID) system may have several underutilized data streams that may be exploited for additional information on user interaction patterns and insulin delivery tendencies. This additional information may be utilized for improved glucose control performance beyond utilizing the EGV readings provided by the CGM. In this example, there may be at least 3 variants of these additional data streams: 1) Utilization of missing EGV values, PISA events, significant jumps in EGV values through calibrations and other CGM characteristic error events to determine possible sensor or pump site issues, and behave accordingly; 2) Utilization of user interaction of the personal diabetes manager or similar interface with the AID system to determine user's level of concern with the current life events and behave accordingly; and 3) Utilization of user bolus patterns to estimate accuracy of user requested boluses and behave accordingly.

One or more examples provide a process that may be used with any additional algorithms or computer applications, such as an AP application as described herein or a third-party artificial pancreas application, which may manage blood glucose levels and provide insulin therapy. Such algorithms may be referred to as an "artificial pancreas" algorithm-based system, or more generally, an artificial pancreas (AP) application, which provides automatic delivery of an insulin based on a blood glucose sensor input, such as that received from a CGM or the like. In an example, the artificial pancreas (AP) application when executed by a processor may enable a system to monitor a user's glucose values, determine an appropriate level of insulin for the user based on the monitored glucose values (e.g., blood glucose concentrations or blood glucose measurement values) and other information, such as user-provided information, such as carbohydrate intake, exercise times, meal times or the like, and take actions to maintain a user's blood glucose value within an appropriate range. The appropriate blood glucose value range may be considered a target blood glucose value of the particular user. For example, a target blood glucose value may be acceptable if it falls within the range of 80 mg/dL to 120 mg/dL, which is a range satisfying the clinical standard of care for treatment of diabetes. However, an AP application as described herein may be able to establish a target blood glucose value more precisely and may set the target blood glucose value at, for example, 110 mg/dL, or the like. As described in more detail with reference to the examples of FIGS. 1-4C, the AP application may utilize the monitored blood glucose values and other information to generate and send a command to a medical device including, for example, a pump, to control delivery of insulin to the user, change the amount or timing of future doses, as well as to control other functions based on the profile of duration of insulin action.

An example implementation of a parameterized safety limits in a closed loop system that is implemented with a permeability layer to allow a dynamic, personalized adaptation of generic, fixed insulin delivery safety constraints is provided. An upper boundary is set so the AP application does not over deliver insulin according to the automatic insulin delivery system. In some examples, the upper boundary does not prevent a user from manually instructing the automatic insulin delivery system to deliver a dose of insulin.

In this example, insulin deliveries in typical closed loop systems are often subject to a wide range of safety constraints. The results of applying these safety constraints may be combined into a fixed upper bound $I_{ub}$ which serves as a hard limit on insulin delivery. The fixed upper bound $I_{ub}$ may be based on a number of variables, such as past blood glucose measurements, past insulin deliveries, blood glucose measurement rate of change, and other factors as shown below. A process for implementing the parameterized safety limits is shown in FIG. 1. In the process 1600, an upper bound may be set for an amount of insulin to be delivered in a period of time (1610). A period of time may, for example, be a day, week, a month, or the like. In the example, the AP application may set the upper bound based on user input or based on a function that takes a number of parameters as inputs.

In an example, the AP application may establish an upper bound Lb that may not be exceeded by insulin delivery recommendations I(t) made by the AP application as shown in the functions below:

$$I(t) \leq I_{ub}(t)$$

$$I_{ub}(t) = f(I(t), G(t), IOB(t), ROC(t))$$

where $I_{ub}(t)$ is a fixed upper bound of insulin that may be delivered over the period of time, and the function $f$ has parameters, where: I(t) is an amount of insulin to be delivered at an approximately given time t, G(t) is current blood glucose measurements at the given time t, IOB(t) is an amount of insulin onboard at the approximate given time t, and ROC(t) is a rate of change of a user's blood glucose at the approximate given time t. In an example, the AP application may obtain blood glucose measurements at regular intervals, which may substantially coincide with the approximate given time. In addition, at or about the regular interval, the AP application may determine and/or calculate recommended insulin delivery (i.e., an amount or dose of insulin to be delivered at approximately the regular interval), insulin onboard and rate of change.

At 1620, the AP application may determine whether the upper bound may be parameterized or "softened." For example, the AP application may parametrize, or soften, these constraints based on known control outcomes. For instance, a soft constraint may be derived from the hard constraint $I_{ub}$ by incorporating an asymptotic approach to a value that is a certain proportion higher than $I_{ub}$:

$$I_{ub,soft}(t) = \frac{a \cdot \log(1+b)}{1 + a \cdot \log(1+b)} \cdot c \cdot I_{ub}(t)$$

the above parametrized version of the hard constraints can dynamically increase or reduce an actual upper bound on insulin delivery applied by an AP application using the algorithm once the hard upper constraint is derived from any control algorithm's standard implementation.

The parameters a, b, and c represent the following characteristics in the soft constraint:

| | |
|---|---|
| a | Rate of convergence of $I_{ub,\ soft}$ to $I_{ub}$ depending on the user dependent parameter b |
| b | Location on the soft constraint curve and may be user dependent |
| c | The threshold for which the soft constraint will asymptotically approach; can allow soft constraints to converge above the hard constraint |

The parameters a and c may be tuned based on inputs to and insulin delivery history the AP application to improve the constraint's robustness against outliers or allow the constraint to be more responsive to parameters set by a user. For example, the parameter b may be utilized to apply various characteristics of the user's current, real-time control outcomes.

In an example, the parameter a may be set to 1 and the parameter c may be set to 2 (1630). In this example, the parameter b may be made dependent on a mean summed square of glucose deviations below target within the past 3 hours as follows:

$$b = \frac{10\sum_{i=0}^{35} \max(50,\ SP - G(t))^2}{36 \cdot 2500}$$

Where, in the above example function, the parameter 10 represents the standard convergence to 130% of the original $I_{ub}(t)$ hard upper bound, and horizon for consideration (36 data points from the current cycle (e.g., 3 hours times 12 blood glucose measurements=36 data points), SP represents the current blood glucose setpoint (i.e., target glucose setpoint) for the user, 2500 represents the summed square of deviations if the measured blood glucose is always at 70 mg/dL and the current blood glucose setpoint (i.e., target glucose setpoint) is at 120 mg/dL, the 50 represents an expected difference between the lower boundary for hypoglycemic risk set at 70 mg/dL and a current blood glucose setpoint (SP—in this example is 120 mg/dL).

In the example, the AP application may, at 1640, receive blood glucose measurement values at given times. The given times may be a period of intervals, such as 5 minute intervals, which coincide with the output of blood glucose measurements from a continuous glucose monitor (shown in another example). The blood glucose measurement values may be received by the AP application over a period of time (e.g., 3 hours—36 data points (12 blood glucose measurements per hour for 3 hours). In addition, the AP application may be operable to store the received blood glucose measurement values in a memory of a personal diabetes management device or the like (shown in another example) until a number (e.g., 36) of blood glucose measurements are received. Alternatively, the AP application may input the received blood glucose measurement values into the maximum function in real time so the parameter b may be determined in real time.

For example, at 1650, the AP application may further determine an actual difference between the measured blood glucose value (G(t)) at the given time and the SP (e.g., 120 mg/dL). After the AP application determines the actual difference between the measured blood glucose value (G(t)) at the given time and the SP (e.g., 120 mg/dL), the AP application in the execution of the max function may determine a final difference. The final difference may be the difference between the expected difference (e.g., 50) of the blood glucose measurement (G(t)) and the current blood glucose setpoint (SP) and the actual difference (SP–G(t)). This final difference may be squared and summed over the 36 data points (from each G(t)) and multiplied by 10 to obtain the numerator. The numerator may be divided by the denominator to obtain the value of parameter b for the period of time.

Upon receipt of the blood glucose measurement values, the AP application may determine the b parameter. In an example calculation of the parameter b, if the blood glucose measurements of a user are consistently below the user's blood glucose set point for the 36 data points, the parameter b is greater than 10, if the blood glucose measurements of the user are consistently equal to the user's blood glucose set point for the 36 data points, the parameter b is equal to 10; and if the blood glucose measurements are consistently above the user's blood glucose set point for the 36 data points, the parameter b is less than 10. In an example, the parameter b may be considered a rate at which the AP application permits the upper bound to be exceeded as the amount of insulin delivered approaches the softened upper bound.

After determination of the parameter b at 1650, the AP application may determine a softened upper bound using the set of parameters a and c and the determined parameter b (1660). Softening the upper bound means, for example, raising a threshold value of the upper bound to allow an amount of insulin to be delivered that is greater than the initially-set upper bound (as in step 1610). In the described specific example, the AP application allows the upper bound to be exceeded by up to, for example, approximately 30% of the user's total daily insulin, if the user did not experience a significant amount of time below 70 mg/dL in the preceding 3 hours (e.g., the user's blood glucose measurements were not below 70 mg/dL for more than 45 minutes out of the 3 hours, or the like). However, since the AP application may recalculate the parameter b and the softened upper bound upon receipt of another blood glucose measurement value, the AP application may rapidly reduce the softened upper bound if the user's blood glucose measurements does fall below 70 mg/dL, which indicates a possibility of hypoglycemic risk. Of course, percentages other than 30%, such as 25%, 50% or the like may be used.

Based on the determined softened upper bound, the AP application, at 1670, may determine a dose of insulin to be delivered to a user. The determined dose of insulin may be an amount of insulin between the set upper bound and the softened upper bound. The determined dose of insulin may cause the amount of insulin delivered in a day to exceed the upper bound set at 1610, but that may lead to the amount of insulin delivered to asymptotically approach the softened upper bound. The AP application may output a signal to a drug delivery device (not shown in this example) containing an instruction to deliver the determined dose of insulin (1680). In this example, the softened upper bound is not exceeded but may be set higher in a subsequent iteration of the process 1600.

This implementation example enables the AP application to dynamically personalize in real-time the upper bound safety constraint based on the user's current diabetes management and blood glucose control outcomes while also allowing a slight violation (i.e., softening) of the hard constraints if the control outcome has been favorable for a period of time, such as 24 hours, 48 hours, or longer.

In other examples, these safety constraints may be made dependent on run-to-run approaches, such as executing the adaptation of the safety constraints once every certain period of data is collected, as alternate forms of adaptivity instead of real time approaches. Prior examples were real-time modifications or updates, while the AP application may also be over time and use instead of set point (SP) may use total daily insulin (TDI). For example, in the function that determines parameter b, the 2500 in the denominator may be replaced with TDI while the maximum tolerance may be 10 units of insulin off from the TDI. Other examples may be for example, proportion of user bolus-to-basal in TDI may also be used.

In this example process of FIG. 1, clinical parameters may be determined with a high confidence of accuracy by the pump, such as total daily insulin (TDI), may be used to modulate the softness (a, c) of the constraints as well as the dependence of the constraint on the parameter (b).

The example of an advanced, on-line updates of glucose prediction models for optimum closed loop artificial pancreas algorithm performance with compatible architectural change that may be operable to improve the formulation of any generic model of insulin and glucose interactions in an insulin delivery system paired with a glucose sensor. A model is typically used to either provide a predicted glucose trajectory for the user, or are incorporated into closed loop insulin delivery algorithms, such as an AP application discussed herein as well as AP applications provided by others, to optimize glucose control outcomes for a respective user. Individual users may begin with a generic model that may be adjusted over time based on the respective individual user's physiology and participation in a diabetes treatment plan that utilizes an automatic insulin delivery (AID) system.

In an example, a standard glucose prediction model of $n^{th}$ order may be implemented to project future glucose values $G_{pred,m}$ from past glucose and insulin delivery values as:

$$G_{pred,m}(k) = b_1 G(k-1) + b_2 G(k-2) + \ldots b_n G(k-n) + a_1 I(k-1) + a_2 I(k-2) + \ldots a_n I(k-n)$$

Where G(k−i)=past blood glucose measurements, G(k)=present glucose measurements, and I(k−i)=past insulin deliveries, and i is 1 to n.

Figure 2:
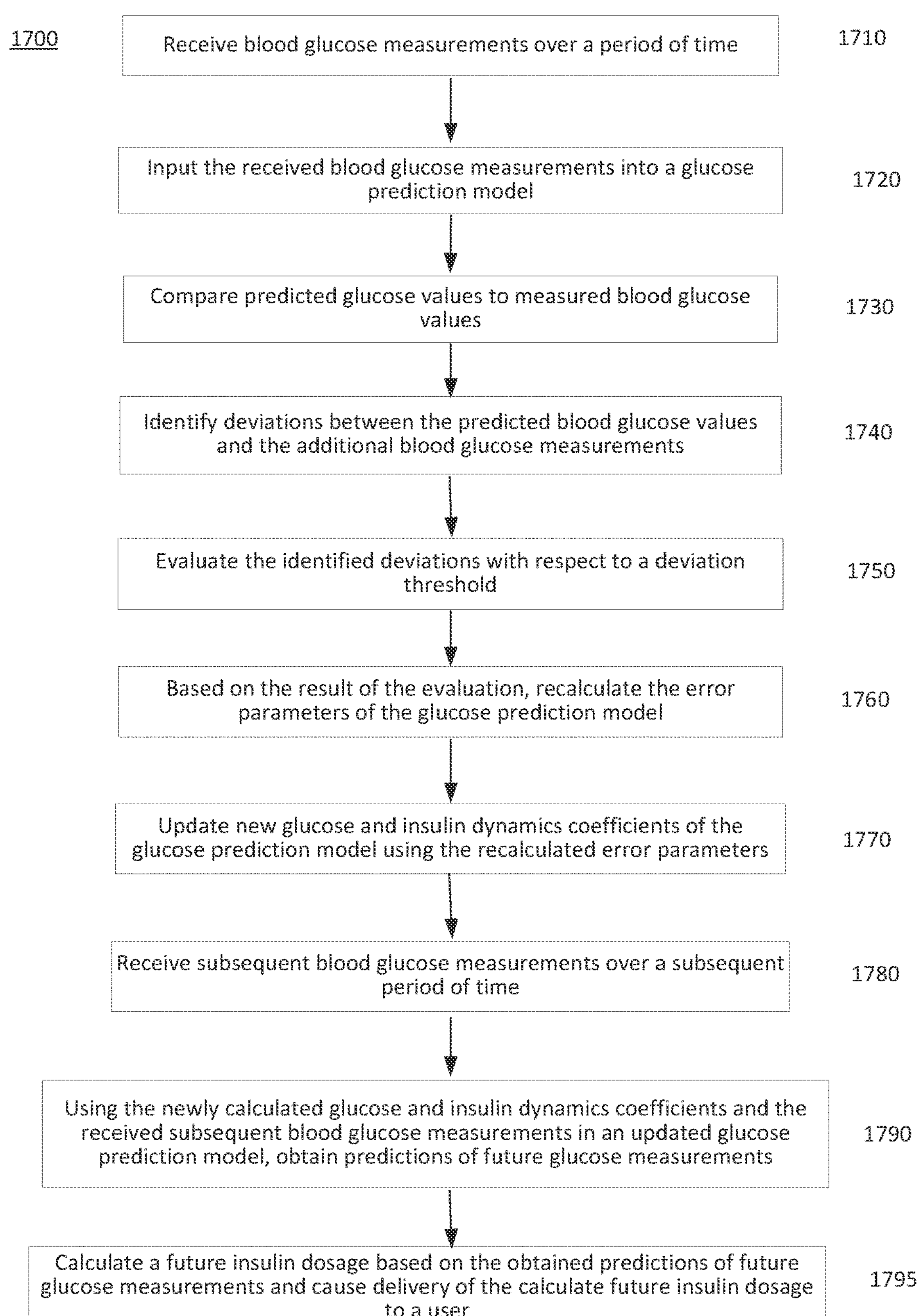
FIG. 2 shows a flow chart of an example of a process for adjustment of a critical parameters of any generic model of glucose and insulin dynamics.

In an example process, such as that shown in FIG. 2, the process 1700 may be implemented to augment or supplement an automatic insulin delivery system that is under control of an artificial pancreas (AP) application. Alternatively, a processor executing programming code may be operable to provide the process 1700 may be implemented on a continuous blood glucose monitor (CGM) or the like (shown in another example). A CGM may make blood glucose measurements approximately every 5 minutes. In an example, a processor executing an AP application on a personal diabetes management device or a processor executing programming code may be operable to implement the process 1700. In the example, the processor may be operable to receive blood glucose measurements over a period of time (1710). For example, the AP application may be executing on a personal diabetes management device may receive the blood glucose measurements via a wireless communication link between the device executing an AP application and a CGM. In the example, the period of time may be one hour, 4 hours, 24 hours, or the like.

At 1720, the received blood glucose measurements may be input into a glucose prediction model $G_{pred,m}$ (k), such as that shown above. The values generated by the glucose prediction model are predictions of future blood glucose values. For example, the predicted blood glucose values may be blood glucose values that are predicted to occur 5, 10, 15, 30, 45 minutes or the like in the future from when the received blood glucose measurements are input into the glucose prediction model. The predicted blood glucose values may be compared to additional blood glucose measurements provided by a CGM (1730). The additional blood glucose measurements may be obtained by a CGM at times that correspond to the times associated with the predicted blood glucose values.

The AP application, when utilizing the process 1700, may identify deviations between the predicted blood glucose values and the additional blood glucose measurements (1740). In an example, the AP application may evaluate the identified deviations with respect to a deviation threshold (1750). Based on the result of the evaluation, the AP application may either take no action or recalculate the error parameters of the glucose prediction model. For example, if the number of identified deviations that exceed the deviation threshold does not exceed a predetermined number, the AP application may take no action. Alternatively, if a predetermined number of identified deviations exceeds the deviation threshold, the process 1700 may recalculate error parameters of the glucose predication model (1760).

The error parameters may be determined using various functions. For example, the error (E(k)) may be the estimated error between the past predictions of the process 1700 and current glucose values that may be assessed by the following estimated error parameter equation:

$$E(k) = \sum_{i=0}^{r} \sum_{m=0}^{p} \left( \frac{G(k-i) - G_{Pred,m}(k-i)}{G(k-i)} \right)^2$$

where r is the history horizon for which the error will be assessed, and p is the prediction horizon of the model that is being assessed. The first term G(k–i) may, for example, be a current glucose value and the second term ($G_{pred,m}$ (k–i)) may be the predicted glucose value. In the estimated error parameter equation, the numerator dividing by the first term that forms the denominator to provide a proportional error for the current cycle. Summation over the prediction (i.e., the first summation of p) time period into the future enables the error to be extrapolated to a point in time in the future. However, p may not extend longer than several cycles into the future. Limiting the limit p in this manner allows the glucose prediction model to reveal any persistent error. In an example, over the last 5 predictions, the limit p may be fixed at 12, which may, for example, be 1 hour's worth of CGM data. In some examples, the limit r may not exceed the value of the limit p. The second summation of r is how many cycles during which the model may make a predictive adjustment. A cycle may be a time period of 1 hour (e.g., 12 blood glucose measurements), 8 hours (e.g., 96 blood glucose measurements), 24 hours (e.g., 288 blood glucose measurements), or the like. For example, if the AP application is operable to adjust the glucose prediction model daily, the limit r may be set to 12 measurements/hour×24 hours=288 measurements, and the parameter k may be a 5 minute measurement interval or the like.

At 1770, the AP application or algorithm may update new glucose and insulin dynamics coefficients of the glucose prediction model using recalculated error parameters. For example, the glucose and insulin dynamics coefficients $b_1 \ldots b_n$ of the glucose prediction model may be updated based on the estimated error parameter E(k):

$$b_{m,new} = b_{m,old} \frac{E(k)}{rp} (\text{bias value})$$

where r is the history horizon for which the error may be assessed, p is the actual prediction horizon for which the model may predict into the future, and (bias value) is a tuning parameter that can be scaled against r and p to adjust how rapidly the model dynamics coefficients can be adjusted.

In this embodiment, the impact of previous glucose values on the model, i.e. the order of the model, may be discounted with increasing residuals, with a lower bound on the model as a zero-order hold from the most recent glucose value. This, for example, reduces the complexity and thus computational cost of the model, allowing for more efficient implementation in real life systems.

After the glucose and insulin dynamics coefficients $b_1 \ldots b_n$ of the glucose prediction model have been updated (1780), subsequent blood glucose measurements may be received over a subsequent period of time.

The AP application or another algorithm may use the newly calculated glucose and insulin dynamics coefficients $b_1 \ldots b_n$ and the received subsequent blood glucose measurements in an updated glucose prediction model, predictions of future glucose measurements may be obtained (1790).

The future glucose measurements may be used in a calculation of a future insulin dosage based on the obtained predictions of future glucose measurements, and, the AP application may cause delivery of the calculated future glucose measurements to a user (1795). The AP application may instruct a drug delivery device to deliver to a user based on a calculation of a future insulin dosage based on the obtained predictions of future glucose measurements.

Additionally, other metrics as the variability of glucose values and/or insulin deliveries above or below certain thresholds based on the user's clinical parameters can also be utilized to better inform the model. For example, frequency of calibration may indicate that the glucose readings were not as reliable as parameterized by the model. In the example, the indication of frequent calibration indicates a lack of confidence by the user because the user for some reason believes the model is not incorrect. As a result, the r parameter or history horizon may be reduced, or alternatively, adjust the bias value.

In other examples, higher order models may also be implemented. In another example, the glucose prediction model as described in the earlier example, may be updated to accommodate glucose and insulin interactions of $n^{th}$ order. The $n^{th}$-order glucose prediction model may be developed to have non-linear dependence depending on the stability characteristics:

$$G_{pred}(k) = b_1 G(k-1)^a + b_2 G(k-2)^b + \ldots \quad b_n G(k-n)^c + a_1 I(k-1)^d + a_2 I(k-2)^e + \ldots \; a_n I(k-n)^z$$

Where G(k–i)=past blood glucose measurements, G(k) =present glucose measurements, I(k–i)=past insulin deliveries, and the exponentials a, b, c, . . . are arbitrary exponents that can also be identified through a similar online identification process as above and be modified in real time. The exponentials allow the incorporation of exponential considerations for indicating the likely greater impact that insulin delivered earlier is currently having on blood glucose measurements.

In further examples, additional insulin effects beyond direct insulin delivery entries may be accounted for by the AP application. In another example of a model of glucose and insulin interactions may be modified to include more advanced insulin effects such as insulin onboard (IOB). In this example, the glucose values may be more impacted by the user's insulin-on-board values (IOB) at each cycle. The resulting generalized equation may be expressed as:

$$G_{pred}(k) = b_1 G(k-1)^a + b_2 G(k-2)^b + \ldots \quad b_n G(k-n)^c + a_1 IOB(k-1)^d + a_2 IOB(k-2)^e + \ldots \; a_n IOB(k-n)^z$$

Where G(k−i)=past blood glucose measurements, G(k) =present glucose measurements, I(k−i)=past insulin deliveries, IOB(k−i)=past IOB determinations, i is 1 to n, and the exponentials a, b, c, . . . are arbitrary exponents that can also be identified through a similar online identification process as above and be modified in real time.

Additional glucose effects beyond auto-regressive incorporation of raw glucose values may also be incorporated into the model. In another example, it is known that the raw blood glucose measurement values from available continuous blood glucose sensors are not as accurate as the rate of change (ROC) estimates of the continuous blood glucose sensors. While information may be gleaned from the raw blood glucose measurement values, a better indication of the effect of the delivered insulin is the rate of change of the raw blood glucose measurement values. Therefore, these models can incorporate the raw rate of change (RoC) values reported by glucose sensors directly to further augment the model:

$$G_{pred}(k) = b_1 ROC(k-1)^a + b_2 ROC(k-2)^b + \ldots\ b_n ROC(k-n)^c + a_1 IOB(k-1)^d + a_2 IOB(k-2)^e + \ldots\ a_n IOB(k-n)^z$$

Where IOB(k−i)=past insulin onboard determinations, ROC (k−i)=past rate of change of glucose, i is 1 to n, and the exponentials a, b, c, . . . are arbitrary exponents that can also be identified through a similar online identification process as above and be modified in real time.

In an example, the automatic insulin delivery algorithms implemented via an AP application or the like in an artificial pancreas system may reside on the insulin delivery vehicles and communicate with continuous glucose monitoring sensors using Bluetooth® Low-Energy protocols. Examples of BLE protocols may use multiple handshakes and points of error before the actual information is sent. By generating a glucose prediction using the above examples of a model, the AP application may be upgraded by implementing the improved model of glucose and insulin interactions as above directly on a continuous glucose monitor (CGM—shown in another example) to avoid the need for the multiple handshakes when providing measurement information. For example, the CGM may utilize the advertising calls available in the BLE protocol to enable insulin deliver by a drug delivery device. By generating the glucose prediction information at the CGM, the CGM may be compatible with multiple drug delivery devices rather than being exclusive to a single drug delivery device.

Further, the recent upgrades to BLE 5.0 means that the typical handshaking approach may be significantly simplified if the CGM may be made to directly advertise its CGM value and RoC values within the advertising packet, which will significantly reduce the points of failure in the communication pathway between a drug delivery device and the CGM thereby improving robustness of the overall diabetes management system. In one or more examples, a CGM may provide blood glucose measurement, estimated rate of change, confidence interval (e.g., how confident the CGM is that the blood glucose measurement is accurate expressed as a range, e.g., BG measurement may be 110, but confidence interval is 100-120) and noise levels.

There are additional inputs that may be implemented to improve the model of insulin/glucose interactions. For instance, clinical outcomes such as the percentage of times that the user spends in safe glycemic range (70-180) within their control may be made as an input to the algorithm. Based on this input, for example, the AP application may determine whether the model's gain (i.e., b coefficients) may be modulated. For example, in the last 24 hours, the user was within range, and as a result, the gain (i.e., b parameters) of the model may be adjusted to a higher value.

In another example, the model may also be extended to incorporate other additional inputs to the system that may be available. For example, inputs such as accelerometer positions (X, Y, Z accelerations), skin temperature, heart rate, pump back pressure (longer time period for insulin to be delivered), frequency of user calibrations of blood glucose measurements, how often a user checks status of system (indicating system is not working properly), and other entries. These may be added to the model to influence real time adjustment. In the example, an input from a skin temperature sensor may provide correlation with respect to determining whether a user is exercising. More specifically, a higher skin temperature at legs as compared to the skin temperature in the abdomen may indicate the user is running. Similarly, elevated inputs values or levels received from a heart rate monitor and an accelerometer (e.g., increased heart rate or increased instantaneous accelerometer values) may indicate exercise. In another example, pump back pressure may indicate that insulin delivery takes longer for the insulin to pass through the interstitial tissue and get into the bloodstream; therefore, the model may be adjusted to respond more slowly to account for the delay in insulin delivery. Meanwhile, an increased number of user status checks may indicate that the automatic insulin delivery (AID) system is not performing optimally and that the user lacks confidence in the AP application settings. As a result, the model parameters may be adjusted in response to the increased number of user status checks.

Figure 3:
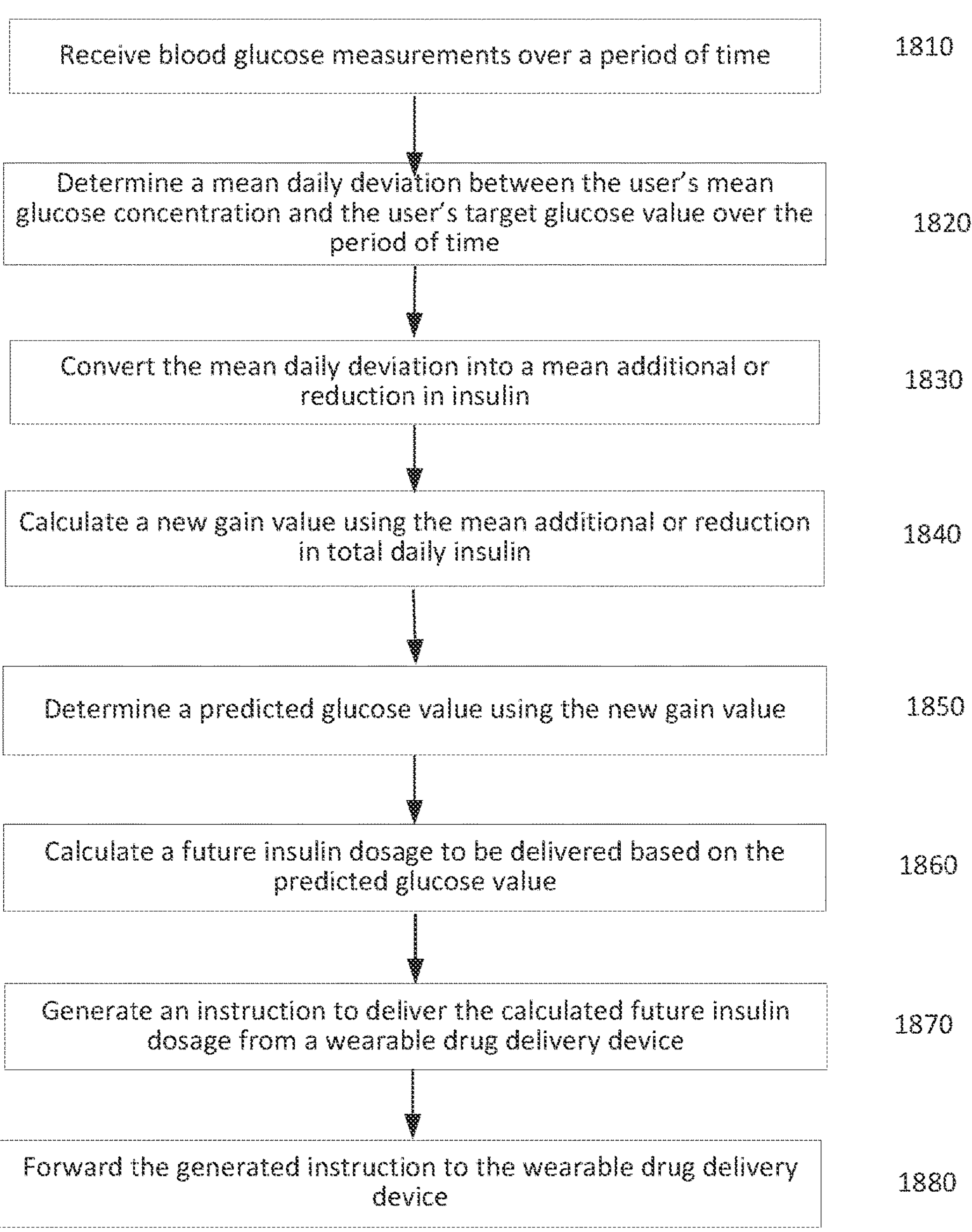
FIG. 3 shows a flow chart of another example of a process for adjustment of a critical parameters of any generic model of glucose and insulin dynamics.

The following example described with reference to FIG. 3 is an implementation of an automatic adjustment of a critical parameters of any generic model of glucose and insulin dynamics that may be utilized in automatic insulin delivery systems for insulin pumps connected with glucose sensors. To accomplish an automatic adjustment of individual model parameters, a number of different parameters may be used, for example, TDI, basal delivery profile, correction factor (e.g., a parameter that represents how much the blood glucose of a user is dropping per 1 unit of insulin delivered to the user), insulin-to-carbohydrate, or other clinical parameters. In the particular example, blood glucose measurements made at different times and an amount of insulin delivered at, or near, the different times may be used as generalized or generic parameters in the determination of a predicted blood glucose value.

A process 1800 may be implemented by a processor or by an AP application. For example, an algorithm, which may be executed by an AP application, may receive blood glucose measurements over a period of time (1810). In the example, the blood glucose measurements may be received from a continuous glucose monitor or the like.

In the example, a model of glucose and insulin dynamics may be subject to a gain K, or a multiplier to the model, as follows:

$$K \cdot G_p(k) = b_1 G(k-1) + b_2 G(k-2) + \ldots\ b_n G(k-n) + a_1 I(k-1) + a_2 I(k-2) + \ldots\ a_n I(k-n)$$

Where K is a generalized gain of this generic model of glucose and insulin values, $G_p$ is a predicted blood glucose measurement, k is an iteration of the blood glucose measurement, $b_n$ are weightings based on estimated correlation between past glucose values and predicted glucose values, G is blood glucose measurement values, and I is an amount of insulin delivered.

In certain examples, the gain K of the model may be defined using various clinical parameters of the user that characterize the user's insulin needs. For example, an advanced TDI determination based on personalized adaptation and adjustment of model gain K may be used.

In the example, the generalized gain K may be dependent on the user's total daily insulin, or TDI parameter, as:

$$K = -c(1-p_1)(1-p_2)\ \ldots\ (1-p_n)\frac{A}{TDI}$$

Where c and A are constants unique to the generic glucose and insulin dynamics model and $p_{1-n}$ are poles of the generic glucose and insulin dynamics model. Values of c and A may be selected based on, for example, the conversion factors between units, insulin infusion rates, insulin infusions, insulin delivery methods, and others, and may have values of, for example, 0.05, 0.06, 0.07, and such for c, and 40, 50, 60, and such for A.

Thus, TDI may be a component of a model of glucose and insulin dynamics given that it represents the total insulin needs of the user.

In a further example, the total daily insulin (TDI) value that is incorporated into the generic glucose and insulin dynamics model may be adjusted in real time based on the user's daily mean blood glucose measurement values. For example, in the process 1800 at 1820, this adjustment may be conducted by calculating a mean daily deviation between the user's blood glucose measurement and the target blood glucose value (each at particular iteration i) as:

$$\bar{D} = \sum_{i=1}^{N} \frac{G(i) - \text{target } (i)}{288}$$

Where N is the total number of available datapoints, i is the specific datapoint, G is the user's blood glucose measurement value and target is the user's target blood glucose value.

In the example, the mean daily deviation $\bar{D}$ provides the average deviation from the user's target glucose. The summation of the user's blood glucose measurement value and target is the user's target blood glucose value provides a total average deviation over the amount of time (e.g., 288 based on N).

The mean daily deviation $\bar{D}$ may be converted into a mean additional insulin or mean reduction in insulin that may be needed to maintain glucose at target based on the user's correction factor parameter:

$$TDI_e = \frac{\bar{D}}{CF}$$

where TDIe is extra/reduced TDI (where extra refers to additional insulin and reduced refers to reduction in insulin), and CF is the correction factor parameter (1830).

In the process 1800, the mean extra or reduction in total daily insulin may be used to calculate a new gain value (1840). The calculated extra/reduced TDIe may be implemented into the generic glucose and insulin dynamics model by being used in a calculation of a new gain value Knew as:

$$K_{new} = -c(1-p_1)(1-p_2)\ \ldots\ (1-p_n)\frac{A}{TDI + TDI_e}$$

In a further example, the adjustment to the gain value may be made more conservative or aggressive based on a factor Q:

$$K_{new,2} = -c(1-p_1)(1-p_2)\ \ldots\ (1-p_n)\frac{A}{TDI + Q \cdot TDI_e}$$

where $K_{new,2}$ refers to the gain value calculated using the factor Q, where Q is a tuning factor that can determine how much the new TDI may be weighted as part of these adjustments.

For example, the Q factor may be adjusted by the percent number (%) of times a user is in the hypoglycemic range (e.g., the user's blood glucose measurement value is less than 70 mg/dL):

$$Q_{hypo} = Q\left(1 - \frac{N_{hypo}}{N}\right)$$

or by glucose variability (e.g., a value representative of how much a user's blood glucose measurements change over time):

$$Q_{var} = Q\left(1 - \frac{GV}{100}\right)$$

Where $Q_{var}$ may be used to increase the robustness of the glucose prediction $G_{pred}$.

The new gain value may be used to determine a predicted glucose value (1850).

The AP application or algorithm may be operable to calculate a future insulin dosage to be delivered based on the predicted glucose values determined using the new gain value (1860). In addition, at 1870, the AP application or algorithm may be operable to generate an instruction to deliver the calculated future insulin dosage from a wearable drug delivery device (not shown in this example). At 1880, the generated instruction may be forwarded by the AP application to the wearable drug delivery device.

In yet another example, an advanced model gain adaptivity of the model gain K may also be provided based on clinical traces which may be updated based on actual clinical outcomes. In the example, the gain K* may be a fixed value that is determined apriori.

For example, the glucose prediction portion of a general model of glucose-insulin dynamics above may be assessed versus known insulin delivery histories to minimize the least square outcomes:

$$K^* = \frac{\sum_{i=1}^{N}(b_1 G(i-1) + b_2 G(i-2) + \ldots\ b_n G(i-n))}{I(i)}$$

In another example, the insulin delivery and glucose histories of a user may be used to calculate an adapted model gain that enables the effects of prandial (meal) periods to be removed which minimizes the impact of carbohydrate ingestions on the predicted glucose measurements.

There are additional alternative examples that may be utilized to further adapt the response of the AP application or algorithm behavior. For instance, a linear incorporation of glucose variability and a percentage (%) of times a user's blood glucose measurements are in the hypoglycemic range (i.e., less than (<) 70 mg/dL) may instead be implemented, for example, by incorporating a weighted horizon approach that discounts periods of very high glucose variability more than periods of low variability.

Further, the incorporation of clinical traces based on model gain can incorporate an iterative optimization approach where areas without significant outside disturbances may be identified within the historical profiles. The values from the areas without significant outside disturbances may be utilized to derive a more accurate modified gain K*.

In an example of a system that utilizes additional sources of data, the additional data may be gleaned from the fact that the users of an automatic insulin delivery (AID) system, which may use an AP application, is a part of closed loop process, and may remain since a user may continuously interact with an AID system throughout their lives. For example, some continuous blood glucose monitors (CGM) may provide in addition to blood glucose measurement values, blood glucose measurement rate of change values, noise factor, and confidence factor, or a combination thereof. The noise factor may be a setting of the sensor that indicates a level of confidence in the blood glucose measurements, and the confidence factor may be a range of confidence related to the provided blood glucose measurement. For example, the noise factor (which may, for example, be an integer value between 1-10 and where 1 may indicate high confidence and 10 may indicate low confidence) may cause the AP application to respond to a provided blood glucose measurement less aggressively. For example, if a blood glucose measurement was 150 mg/dL and the noise factor may indicate a confidence value of 9, the AP application or algorithm may modify the dose of insulin to be delivered based on the noise factor to be lower than expected, indicating a lower confidence in the glucose value due to the high level of noise. In contrast to the noise factor, the confidence factor is a tolerance level expressed as a range of the blood glucose measurement values. For example, the CGM may also provide a range of blood glucose measurement values, such as 115-130 mg/DL that indicate the confidence the CGM has in the current blood glucose measurement value.

In another example, the CGM may provide a measure (or indication) of pressure to an AP application. The provided pressure measurement may indicate that the system is experiencing pressure-induced sensor attenuation (PISA). The PISA may be caused by, for example, a user sleeping on the CGM, which may affect the ability of the CGM to accurately measure blood glucose. In the example, the AP application may evaluate the pressure measurements and determine whether the sensor is experiencing PISA and the extent to which the PISA is affecting a user's blood glucose measurement values.

In a further example, the CGM may occasionally fail to provide a blood glucose measurement to the AP application. The AP application may monitor the number of times that the CGM fails to deliver the blood glucose measurement (i.e., "missing blood glucose measurements"). In an example, the AP application may identify significant increases in missing blood glucose measurement values by tracking an increase in the frequency of calibrations and occurrences of other CGM characteristic error events. The AP application may use the identified increases in missing blood glucose measurements and occurrences of other CGM characteristic error events to determine possible CGM sensor or drug delivery device (i.e., pump) site issues (such as buildup of scar tissue or the like). In response to determining the possible CGM sensor or drug delivery device site issues, the AP application may respond accordingly. For example, the AP application may generate prompts requesting a user to relocate either the CGM sensor or drug delivery device to another site on the user's body.

In the example, the presence of faults within the available data themselves may be utilized as another source of data. For example, the faults may include missing EGV values, PISA events, and or non-physiological jumps in EGV values which can occur due to user calibrations or sensor noise. In response to the missing electronic glucose values (EGV), PISA events, and/or significant jumps in interaction with the AP application or CGM (for example, more frequent calibrations, other noise, or the like), the AP application may become more conservative in the delivery of insulin for the purpose of reducing blood glucose or allowing blood glucose to rise. In an example, the average rate of incidence of these occurrence of the faults may be characterized for each individual user over multiple usage sessions with an AID system managed by an AP application.

In another example, if faults occur more often compared to a standard rate of incidence (determined across a large number of users of the AID system), the high occurrence of faults may indicate an abnormal site issue or change in user behavior which may necessitate a more conservative automated insulin delivery behavior.

Figure 4A:
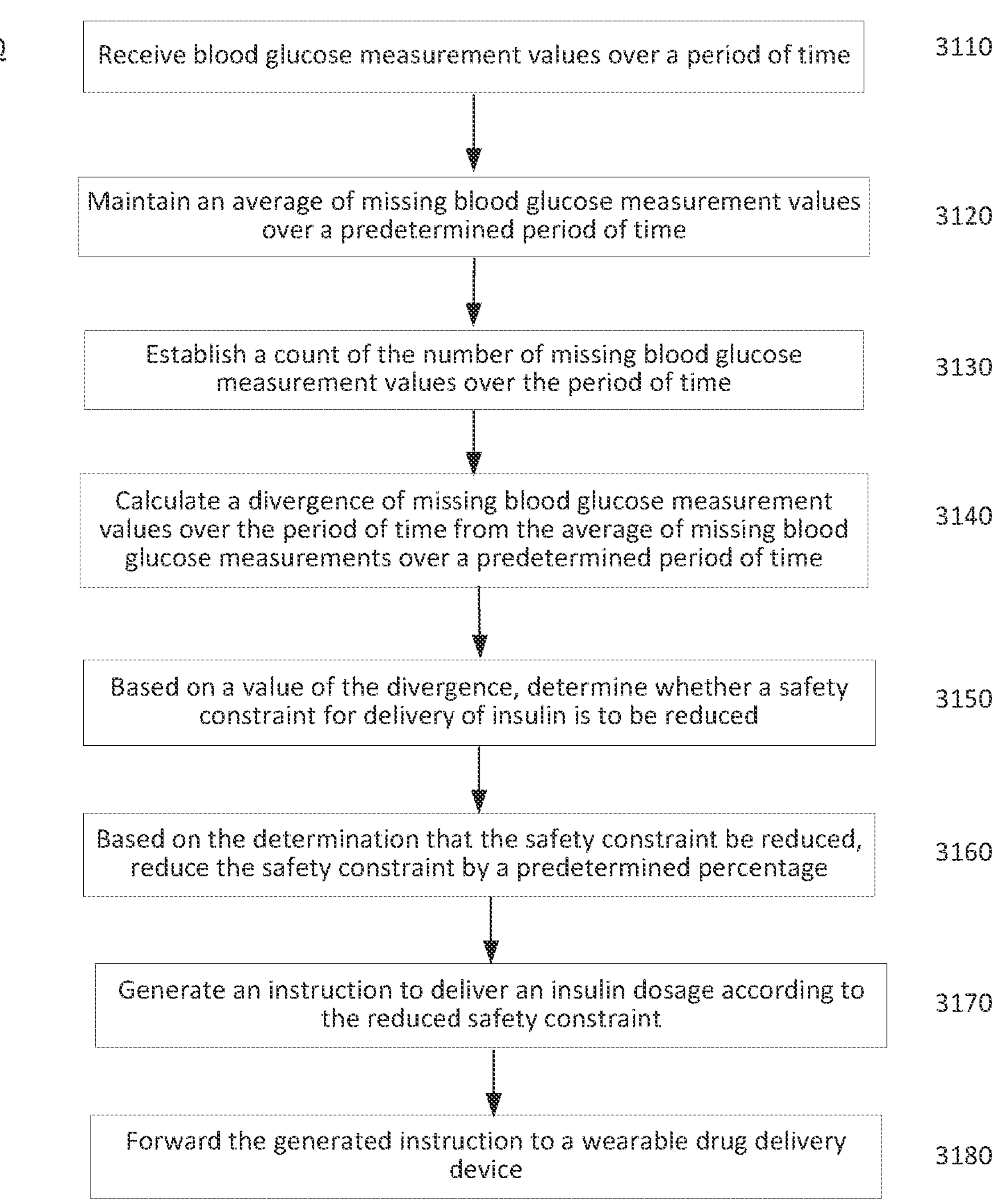
FIG. 4A illustrates a flow chart of another example of a process for adjusting a safety constraint based on missing blood glucose measurement.

An example of a process 3100 that accounts for the missing blood glucose measurements is illustrated in FIG. 4A. In the example of FIG. 4A, the AP application may receive an AP application or an algorithm executing on a processor may identify a blood glucose measurement as missing when the blood glucose measurement is not received at an expected time (e.g., every 5 minutes or the like), or within some time tolerance before or after the expected time. An AP application or an algorithm may be operable to receive blood glucose measurements from a blood glucose monitor over a period of time (3110). For example, the AP application may be executing on a personal diabetes management device or the algorithm may be executing on a drug delivery device. The respective AP application or algorithm may be further operable to maintain an average of missing blood glucose measurements over a predetermined time period (3120). The respective AP Application or algorithm may be operable to establish a count of the number of missing blood glucose measurements over the period of time (3130). For example, a predetermined number of blood glucose measurements (e.g., electronic glucose values (EGV)) are expected to be missing due to various reasons, such as loss of communication between the CGM and the AP application (or algorithm), noisy sensor site, sensor warmup, or the like.

At 3140, the AP application or algorithm may be operable to Calculate a divergence of missing blood glucose measurements over the period of time from the average of missing blood glucose measurements over a predetermined time period. In an example, the divergence in missing blood glucose measurements $D_m$ may be calculated as based on the following $$D_m(i) = \frac{M(i) - \overline{M}}{\overline{M}}$$

where M represents the number of missing blood glucose measurements values per a period of time, M.dash is an average number of missing blood glucose measurements values (EGV) per a predetermined time period, and (i) is each missing blood glucose measurements value (EGV) over the predetermined time period (which may equal the current cycle, such 24 hours or the like).

Based on a value of the divergence, the AP application or algorithm may be operable to determine whether a safety constraint for delivery of insulin is to be reduced (3150). In the example, if a value of Dm is greater than, for example, approximately 1.5 (which may be tuned based on age, insulin sensitivity, activity such as swimming, or other activity), the AP application or algorithm may interpret a greater divergence as an indication that the user's pump or sensor insertion sites may be sub optimal for the current usage session, and thus may desire to modify its behavior.

In response, the AP application or algorithm controlling the automated insulin delivery system may reduce a safety constraint by a predetermined percentage due to the additional available information regarding the user's current system setup (3160). A safety constraint may, for example, be one or more of a maximum amount of total daily insulin to be delivered to a user, a limit on a basal rate of insulin to be delivered, a limit based on the user's insulin-on-board value, a limit based on the user's glucose concentration value, or the like. The predetermined percentage may be 3%, 10%, 15%, or the like.

The AP application or algorithm may generate an instruction to deliver an insulin dosage according to the reduced safety constraint (3170). At 3180, the AP application or algorithm may forward the generated instruction to a wearable drug delivery device.

In another example, the number of times the user may activate the system to view their current system status can indicate the user's level of concern, awareness of their metrics, and likelihood of addressing risk events. An ultimate goal of an AID system is to allow the users to minimize their need for checking the status of their diseases. Therefore, in the examples, the average user interaction rate with an external interface device to the system, such as the PDM, may be assessed. Then, if the user interacts with the system at a significant higher rate than this average interaction rate over a short period, the AID system may determine that the user feels they are in a state where there is a risk of sub optimal control (such as exercise, or large feasts), without the need for additional user interaction. Accordingly, in addition to the data streams that are directly related to current data streams available within the system (such as insulin delivery history, known EGV values, user requested boluses and the like), the occurrence of user interactions themselves can also be utilized to characterize the user's behavior, the implications of the user's behavior, and the AID systems performance.

Figure 4B:
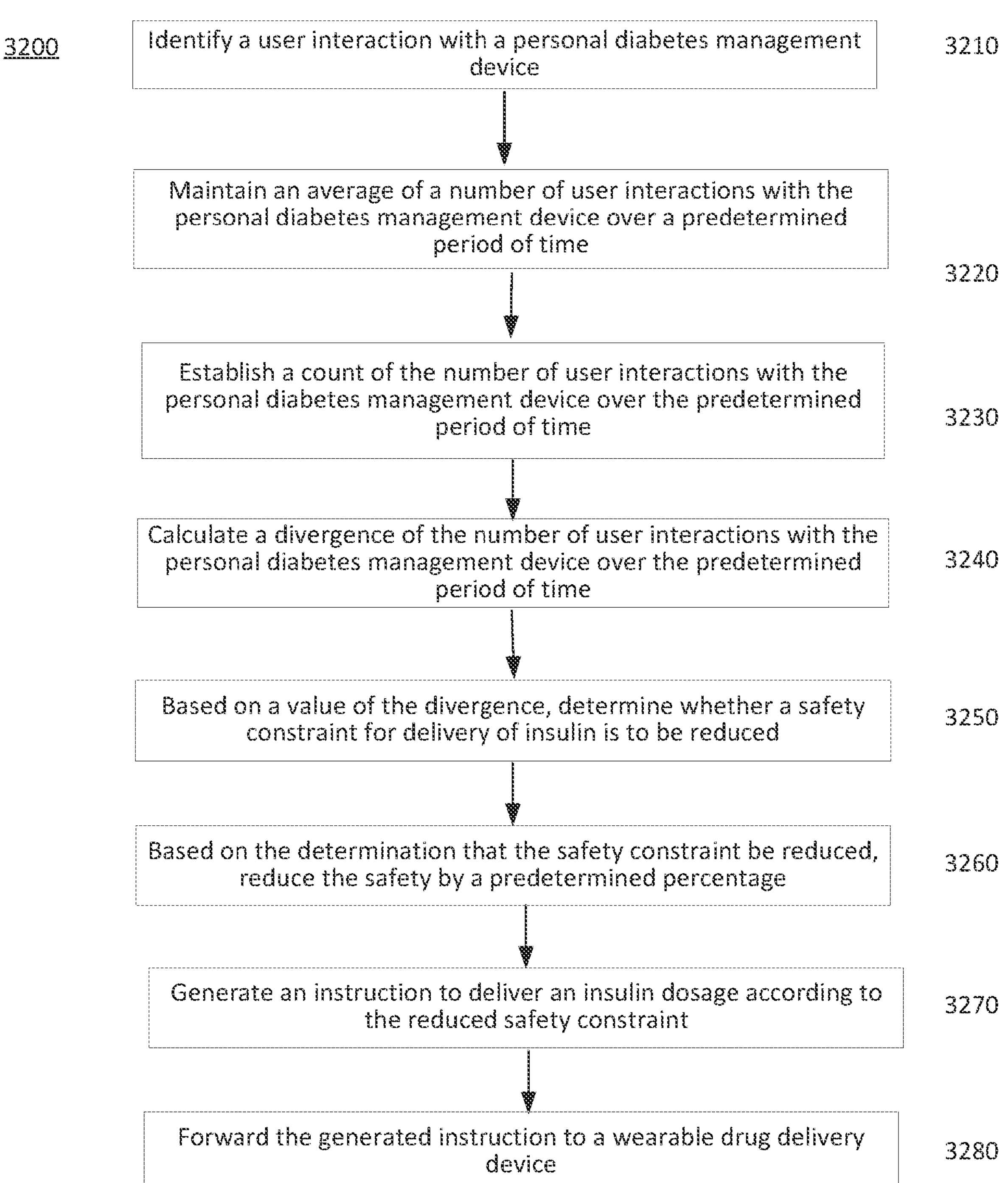
FIG. 4B illustrates a flow chart of another example of a process for adjusting a safety constraint based on user interactions with the system.

In another example as shown in FIG. 4B, the user interaction with an AID device interface, for example, on a personal diabetes management device may be utilized to determine a user's level of concern and likelihood of user intervention. FIG. 4B illustrates an example of a process that utilizes instances of user interaction with an AID device to make insulin dosing determinations.

In the example process 3200 of FIG. 4B, an AP application or algorithm executing on a PDM or drug delivery device, or both a PDM and a drug delivery device may be operable, at 3210, to identify a user interaction with a personal diabetes management device.

The AP application or algorithm executing on a PDM or drug delivery device, or both a PDM and a drug delivery device may be operable maintain an average of a number of user interactions with the personal diabetes management device over a predetermined time period (3220).

The AP application or algorithm may be further operable to establish a count of the number of user interactions with the personal diabetes management device over the predetermined time period (3230). Similar to the equation for determining the divergence of the number of missing EGVs from the average number of missing EGVs described above with respect to FIG. 4A, the divergence function may be used to calculate the divergence of the number of user interactions with the diabetes management system over a period of time from the average number of user interactions with the diabetes management system over the period of time (3240).

In an example, the divergence in user interactions DUserInt may be calculated as based on the following:

$$D_{UserInt}(i) = \frac{MUI(i) - \overline{MUI}}{\overline{MUI}}$$

where MUI represents the number of user interactions per a period of time, MUI.dash is an average number of user interaction per a predetermined time period, and (i) is an occurrence of a user interaction over the predetermined time period (which may equal the current cycle, such 24 hours or the like).

Based on a value of the divergence, the AP application or algorithm may be operable to determine whether a safety constraint for delivery of insulin is to be reduced (3250). In the example, if a value of Dm is greater than, for example, approximately 1.5 (which may be tuned based on age, insulin sensitivity, activity such as swimming, or other activity), the AP application or algorithm may interpret a greater divergence as an indication that the user's pump or sensor insertion sites may be sub optimal for the current usage session.

In response, the AP application or algorithm controlling the automated insulin delivery system may reduce a safety constraint due to the additional available information regarding the user's current system setup (3260). A safety constraint may, for example, be one or more of a maximum amount of total daily insulin to be delivered to a user, a limit on a basal rate of insulin to be delivered, a limit based on the user's insulin-on-board value, a limit based on the user's glucose concentration value, or the like. The AP application or algorithm may generate an instruction to deliver an insulin dosage according to the reduced safety constraint (3270). At 3280, the AP application or algorithm may forward the generated instruction to a wearable drug delivery device.

Figure 4C:
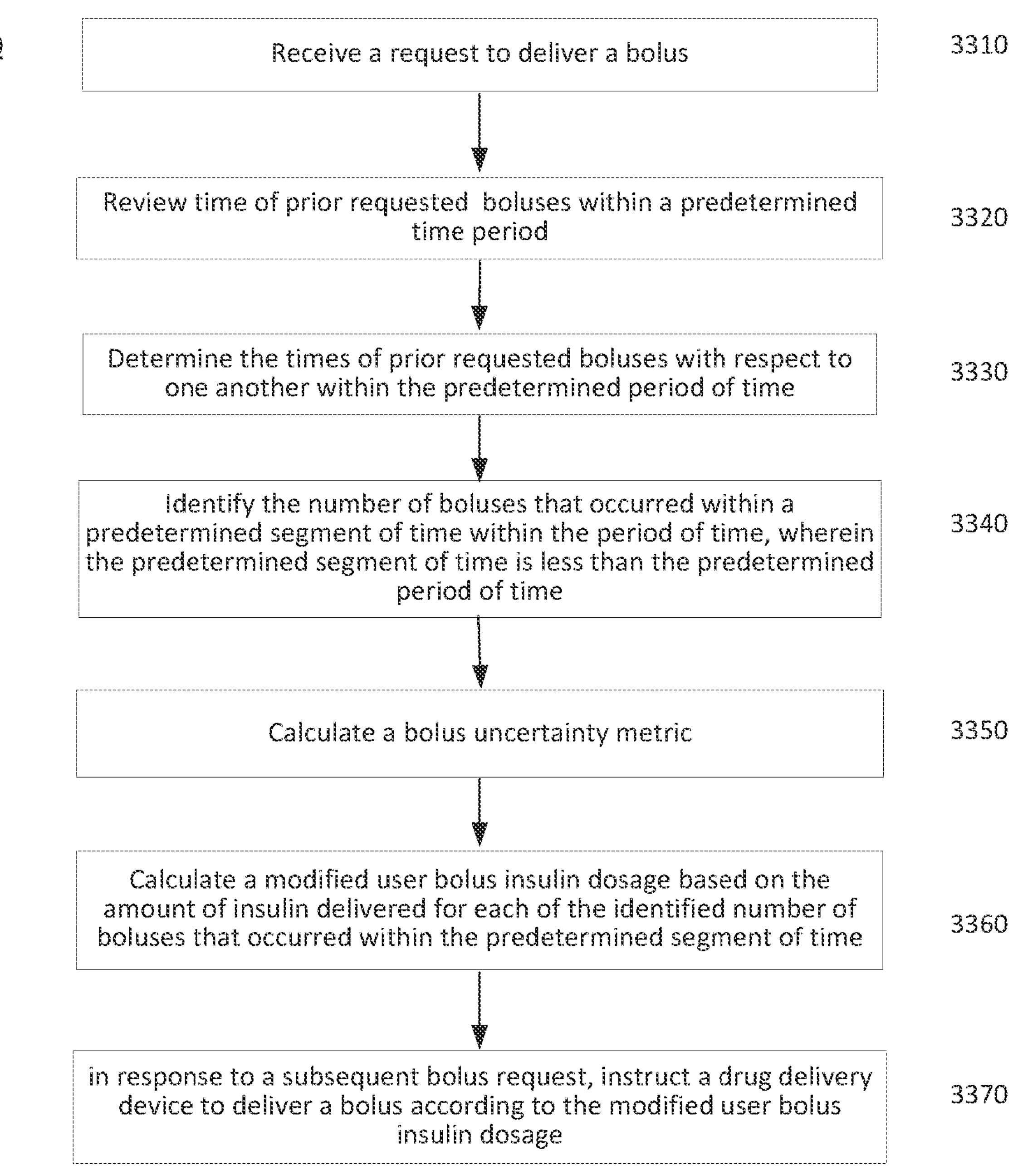
FIG. 4C illustrates a flow chart of another example of a process for adjusting a bolus uncertainty metric used in the calculation of a bolus insulin dose.

In another example, such as that shown in FIG. 4C, an AP application or algorithm may utilize user bolusing patterns to determine a relative accuracy of the user's bolusing needs. A bolus may be considered any dosage of insulin that is provided in response to a request by a user. FIG. 4C illustrates an example process for modifying a user's insulin bolus dosage. For example, a user may bolus multiple times within a short period of time rather than just once for each user interaction with the AP application or drug delivery device. For example, in the process 3300, an AP application or a drug delivery device may be operable to response to a user's bolus request. In the process 3300, the AP application or an algorithm executing on the drug delivery device may receive a request to deliver a bolus (3310). The bolus request may be, for example, due to a user's desire to compensate for a mis-estimation of their insulin needs with their initial bolus, the user's desire to ingest snacks having additional carbohydrates beyond the user's original needs, exercise bolus, or any other reason that a user may want to receive a bolus dosage. In the example of the user's desire to ingest snacks with additional carbohydrates, the additional carbohydrates may be captured as an average bolus uncertainty metric. In the example process 3300, the AP application or algorithm may review, at 3320, a time that prior boluses were requested and whether any of the prior boluses were requested within a predetermined time period prior to the receipt of the request to deliver a bolus (at 3310). For example, the AP application or algorithm may consider a possibility that any boluses that occur within the expected insulin peak time of 90 minutes may be considered as a single bolus. In an example, the predetermined time period may be substantially equal to an expected insulin peak time, which may be 90 minutes, 105 minutes, or the like. The predetermined time period may be a number of set time windows of the same amount of time (e.g., 90 minutes, 105 minutes or the like), such as 8 am to 9:30 am, 12 pm to 1:30 pm, 1:30 pm to 3 pm, and so on. Alternatively, the predetermined time period may be a sliding window of a set time (e.g., 90 minutes, 105 minutes, or the like) that may begin at a particular time such as 6 am and continue to an expected bedtime for the user. The AP application or algorithm may determine the times of prior requested boluses with respect to one another within the predetermined period of time (3330).

The AP application or algorithm identify the number of boluses that occurred within a predetermined segment of time within the period of time, wherein the predetermined segment of time is less than the predetermined time period (3340). Using the times of prior boluses and the number of boluses, the AP application or algorithm may calculate a bolus uncertainty metric (3350). The average bolus uncertainty metric may be used by the AP application (or algorithm) as a constraint or loosening in the evaluation of when to deliver insulin following these types of boluses (e.g., supplemental meal boluses, exercise boluses and the like).

In an example, an average bolus uncertainty metric $B_{un}$ may be calculated as:

$$B_{un} = \frac{\sum_{i=1}^{N_{bol,a}} N_{bol,un}}{N_{bol,a}}$$

where $N_{bol,un}$ may be characterized as a number of other bolus events that occurred within 90 minutes around any single bolus event, and $N_{bol,a}$ is an aggregate of the number of bolus events. If $B_{un}$ is based on one bolus, $B_{un}$ may be called a bolus uncertainty metric.

In response to the calculated bolus uncertainty metric, the AP application or algorithm may calculate a modified user bolus insulin dosage based on the amount of insulin delivered for each of the identified number of boluses that occurred within the predetermined segment of time (3360). In response to the modified user bolus insulin dosage, at 3370, the AP application or algorithm, may generate commands for the drug delivery device to deliver the modified user bolus insulin dosage in response to a subsequent bolus request.

In a specific example, in the above formulation of $B_{un}$, the function double counts any one pair of boluses that occur within 90 minutes; therefore, a $B_{un}$ value of greater than 2 may be considered a high likelihood that the user's boluses generally are insufficient to cover the user's insulin needs. In response to the $B_{un}$ value being greater than 2, the AP application or algorithm that contributes to the management of the AID system may increase insulin deliveries based on the value of the $B_{un}$ parameter. For example, the modified user bolus insulin dosage calculated at 3360 may be increased based on the value of the $B_{un}$ parameter.

In another example, parameter identification techniques may be utilized to determine the importance of each additional parameter, and possibly generate a model of the user's behavior and their expected impact on AID outcomes. Further, the importance of each proposed data stream may be evaluated in real time to provide a broader overall picture of the user's diabetes care regimen beyond simple insulin delivery and glucose traces.

FIGS. 1-4C show a flowcharts of process examples for updating a duration of insulin action setting.

In the examples of FIGS. 1-4C, the example processes may be implemented by programming code, such as an AP application or an algorithm, that is executed by a processor. The AP application or algorithm when executed by a processor may utilize inputs and calculations as described with respect to the foregoing examples.

Figure 5:
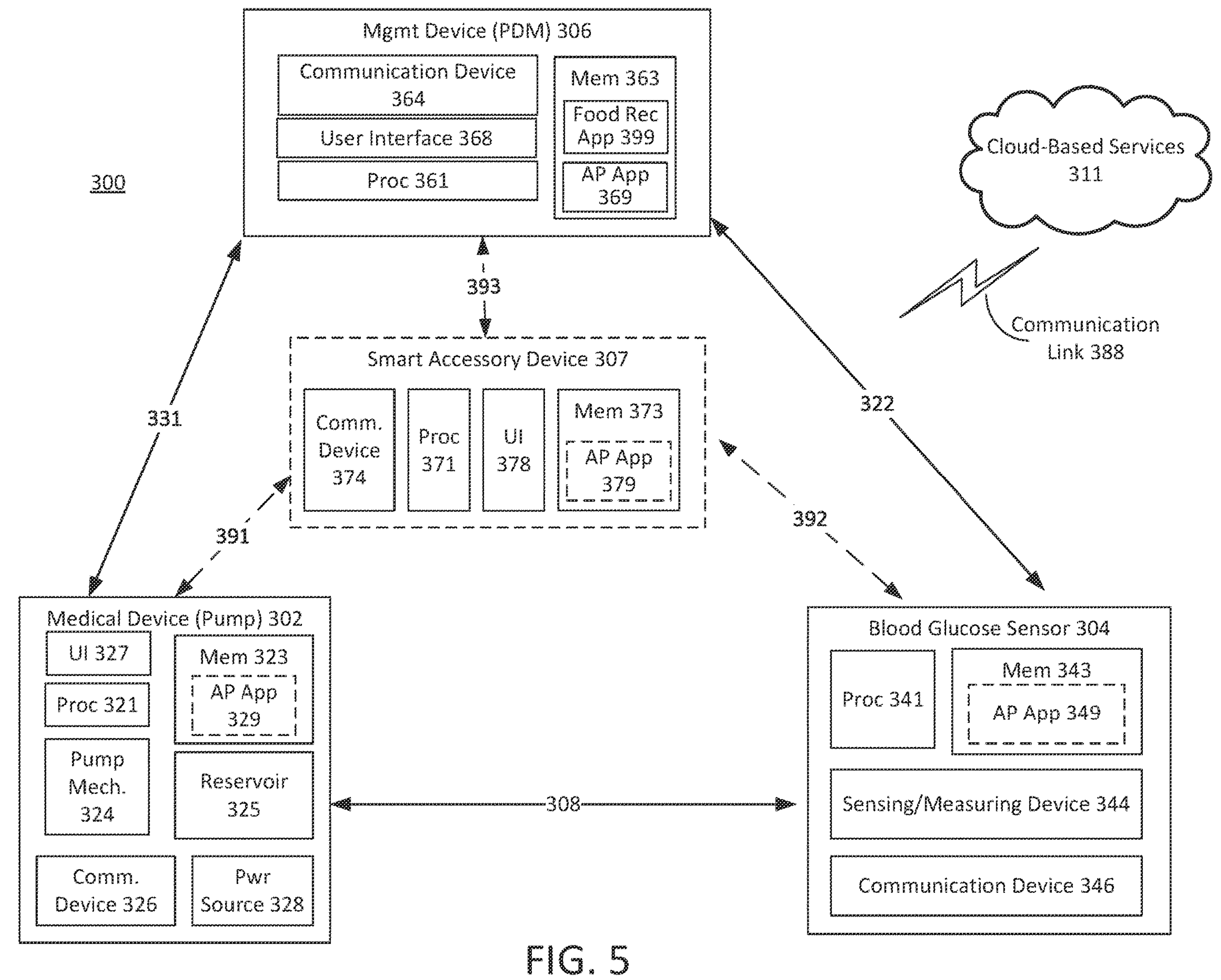
FIG. 5 illustrates a functional block diagram of drug delivery system suitable for implementing the example processes and techniques described herein.

It may be helpful to discuss an example of a drug delivery system that may implement the process example of FIGS. 1-4C. FIG. 5 illustrates an example of a drug delivery system 300.

The drug delivery system 300 may be operable to implement the process examples illustrated in FIGS. 1-4C by executing an AP application or algorithm that includes functionality to determine when to softened upper bounds of insulin delivery and how much to soften the upper bound; predict future blood glucose measurement values by calculating deviations between predicted blood glucose measurement values and additional blood glucose measurement values; determining a gain parameter for use with a model of predicting a user's blood glucose measurement values and determining future insulin dosages; determine safety constraints based on an evaluation of missing blood glucose measurement values; determine safety constraints based on an evaluation of a user's increased interaction with an automatic insulin delivery device; and calculate a bolus uncertainty metric to determine an amount of insulin to be provided in a bolus dosage in response to a bolus request.

The drug delivery system 300 may be an automated drug delivery system that may include a medical device (pump) 302 (also referred to as "a drug delivery device" or "a wearable drug delivery device"), a blood glucose sensor 304 (also referred to as "a continuous glucose monitor" or "a blood glucose measurement device"), and a management device (PDM) 306. The system 300, in an example, may also include a smart accessory device 307, which may be operable to communicate with the other components of system 300 either via a wired or wireless communication link, such as 391, 392 or 393.

In an example, the medical device 302 may be attached to the body of a user, such as a patient or diabetic, and may deliver any therapeutic agent, including any drug or medicine, such as insulin, morphine or the like, to the user. The medical device 302 may, for example, be a wearable device worn by the user. For example, the medical device 302 may be directly coupled to a user (e.g., directly attached to a body part and/or skin of the user via an adhesive or the like). In an example, a surface of the medical device 302 may include an adhesive (not shown) to facilitate attachment to a user.

The medical device 302 may include a number of components to facilitate automated delivery of a drug (also referred to as a therapeutic agent) to the user. The medical device 302 may be operable to store the drug (i.e., insulin) and to provide the drug to the user. The medical device 302 is often referred to as a pump, or an insulin pump, in reference to the operation of expelling insulin from the reservoir 325 for delivery to the user. While the examples refer to the reservoir 325 storing insulin, the reservoir 325 may be operable to store other drugs or therapeutic agents, such as morphine or the like, that are suitable for automated delivery.

In various examples, the medical device 302 may be an automated, wearable drug delivery device. For example, the medical device 302 may include a reservoir 325 for storing the drug (such as insulin), a needle or cannula (not shown) for delivering the drug into the body of the user (which may be done subcutaneously, intraperitoneally, or intravenously), and a pump mechanism (mech.) 324, or other drive mechanism, for transferring the drug from the reservoir 325, through a needle or cannula (not shown), and into the user. The pump mechanism 324 may be fluidly coupled to reservoir 325, and communicatively coupled to the medical device processor 321. The medical device 302 may also include a power source 328, such as a battery, a piezoelectric device, or the like, for supplying electrical power to the pump mechanism 324 and/or other components (such as the processor 321, memory 323, and the communication device 326) of the medical device 302. Although not shown, an electrical power supply for supplying electrical power may similarly be included in each of the sensor 304, the smart accessory device 307 and the management device (PDM) 306.

The blood glucose sensor 304 may be a device communicatively coupled to the processor 361 or 321 and may be operable to measure a blood glucose value at a predetermined time interval, such as every 5 minutes, or the like. The blood glucose sensor 304 may provide a number of blood glucose measurement values to the AP applications operating on the respective devices (e.g., 329, 349 369, or 379).

The medical device 302 may provide the insulin stored in reservoir 325 to the user based on information (e.g., blood glucose measurement values, predicted future blood glucose measurements, evaluations based on a user request for a bolus, an user interaction with PDM 306, medical device 302, sensor 304 or smart accessory device 307), evaluations of missing blood glucose measurements and the other information provided by the sensor 304, smart accessory device 307, and/or the management device (PDM) 306. For example, the medical device 302 may contain analog and/or digital circuitry that may be implemented as a processor 321 (or controller) for controlling the delivery of the drug or therapeutic agent. The circuitry used to implement the processor 321 may include discrete, specialized logic and/or components, an application-specific integrated circuit, a microcontroller or processor that executes software instructions, firmware, programming instructions or programming code (enabling, for example, the artificial pancreas application (AP App) 329 as well as the process examples of FIGS. 1-4C) stored in memory 323, or any combination thereof. For example, the processor 321 may execute a control algorithm, such as an artificial pancreas application 329, and other programming code that may make the processor 321 operable to cause the pump to deliver doses of the drug or therapeutic agent to a user at predetermined intervals or as needed to bring blood glucose measurement values to a target blood glucose value. In an example, the AP application (App) 329 may include programming code that is operable upon execution by the processor 321 to provide the example processes for adjusting or modifying duration of insulin action settings, confidence values, insulin delivery settings, storing blood glucose measurement values in memory, or the like as described with reference to FIGS. 1-4C. The size and/or timing of the doses may be programmed, for example, into an artificial pancreas application 329 by the user or by a third party (such as a health care provider, medical device manufacturer, or the like) using a wired or wireless link, such as 331, between the medical device 302 and a management device 306 or other device, such as a computing device at a healthcare provider facility. In an example, the pump or medical device 302 is communicatively coupled to the processor 361 of the management device via the wireless link 331 or via a wireless link, such as 391 from smart accessory device 307 or 308 from the sensor 304. The pump mechanism 324 of the medical device 302 may be operable to receive an actuation signal from the processor 361, and in response to receiving a command signal or actuation signal, expel insulin from the reservoir 325 based on the evaluations and process steps performed in the process examples of FIGS. 1-4C.

In an operational example, the AP application 369 may be executing in the management device 306 and control delivery of insulin. For example, the AP application 369 may be operable to determine timing of an insulin dose and may output a command signal to the medical device 302 that actuates the pump mechanism 324 to deliver insulin dose based on the evaluations and process steps performed in the process examples of FIGS. 1-4C.

The other devices in the system 300, such as management device 306, smart accessory device 307 and sensor 304, may also be operable to perform various functions including controlling the medical device 302. For example, the management device 306 may include a communication device 364, a processor 361, and a management device memory 363. The management device memory 363 may store an instance of the AP application 369 that includes programming code, that when executed by the processor 361 provides the process examples described with reference to the examples of FIGS. 1-4C. The management device memory 363 may also store programming code for providing the process examples described with reference to the examples of FIGS. 1-4C.

The smart accessory device 307 may be, for example, an Apple Watch®, other wearable smart device, including eyeglasses, provided by other manufacturers, a global positioning system-enabled wearable, a wearable fitness device, smart clothing, or the like. Similar to the management device 306, the smart accessory device 307 may also be operable to perform various functions including controlling the medical device 302. For example, the smart accessory device 307 may include a communication device 374, a processor 371, and a memory 373. The memory 373 may store an instance of the AP application 379 that includes programming code for providing the process examples described with reference to the examples of FIGS. 1 and 2. The memory 373 may also as store programming code and be operable to store data related to the AP application 379. The sensor 304 of system 300 may be a continuous glucose monitor (CGM) as described above, that may include a processor 341, a memory 343, a sensing or measuring device 344, and a communication device 346. The memory 343 may, for example, store an instance of an AP application 349 as well as other programming code and be operable to store data related to the AP application 349 and process examples described with reference to FIGS. 1-4C. The AP application 349 may also include programming code for providing the process examples described with reference to the examples of FIGS. 1-4C.

Instructions for determining the delivery of the drug or therapeutic agent (e.g., as a bolus dosage) to the user (e.g., the size and/or timing of any doses of the drug or therapeutic agent) may originate locally by the medical device 302 or may originate remotely and be provided to the medical device 302. In an example of a local determination of drug or therapeutic agent delivery, programming instructions, such as an instance of the artificial pancreas application 329, stored in the memory 323 that is coupled to the medical device 302 may be used to make determinations by the medical device 302. In addition, the medical device 302 may be operable to communicate with the cloud-based services 311 via the communication device 326 and the communication link 388.

Alternatively, the remote instructions may be provided to the medical device 302 over a wired or wireless link (such as 331) by the management device (PDM) 306, which has a processor 361 that executes an instance of the artificial pancreas application 369, or the smart accessory device 307 (via communication link 391), which has a processor 371 that executes an instance of the artificial pancreas application 369 as well as other programming code for controlling various devices, such as the medical device 302, smart accessory device 307 and/or sensor 304. The medical device 302 may execute any received instructions (originating internally or from the management device 306) for the delivery of the drug or therapeutic agent to the user. In this way, the delivery of the drug or therapeutic agent to a user may be automated.

In various examples, the medical device 302 may communicate via a wireless link 331 with the management device 306. The management device 306 may be an electronic device such as, for example, a smart phone, a tablet, a dedicated diabetes therapy management device, or the like. The management device 306 may be a wearable wireless accessory device. The wireless links 308, 331, 322, 391, 392 and 393 may be any type of wireless link provided by any known wireless standard. As an example, the wireless links 308, 331, 322, 391, 392 and 393 may enable communications between the medical device 302, the management device 306 and sensor 304 based on, for example, Bluetooth®, Wi-Fi®, a near-field communication standard, a cellular standard, or any other wireless optical or radio-frequency protocol.

The sensor 304 may be a glucose sensor operable to measure blood glucose and output a blood glucose value or data that is representative of a blood glucose value. For example, the sensor 304 may be a glucose monitor or a continuous glucose monitor (CGM). The sensor 304 may include a processor 341, a memory 343, a sensing/measuring device 344, and communication device 346. The communication device 346 of sensor 304 may include one or more sensing elements, an electronic transmitter, receiver, and/or transceiver for communicating with the management device 306 over a wireless link 322 or with medical device 302 over the link 308. The sensing/measuring device 344 may include one or more sensing elements, such as a glucose measurement, heart rate monitor, or the like. The processor 341 may include discrete, specialized logic and/or components, an application-specific integrated circuit, a microcontroller or processor that executes software instructions, firmware, programming instructions stored in memory (such as memory 343), or any combination thereof. For example, the memory 343 may store an instance of an AP application 349 that is executable by the processor 341.

Although the sensor 304 is depicted as separate from the medical device 302, in various examples, the sensor 304 and medical device 302 may be incorporated into the same unit. That is, in various examples, the sensor 304 may be a part of the medical device 302 and contained within the same housing of the medical device 302 (e.g., the sensor 304 may be positioned within or embedded within the medical device 302). Glucose monitoring data (e.g., measured blood glucose values) determined by the sensor 304 may be provided to the medical device 302, smart accessory device 307 and/or the management device 306 and may be used to perform the functions and deliver doses of insulin for automated delivery of insulin by the medical device 302 as described with reference to the examples of FIGS. 1-4C.

The sensor 304 may also be coupled to the user by, for example, adhesive or the like and may provide information or data on one or more medical conditions and/or physical attributes of the user. The information or data provided by the sensor 304 may be used to adjust drug delivery operations of the medical device 302.

In an example, the management device 306 may be a computing device operable to manage a personal diabetes treatment plan via an AP application or an algorithm. The management device 306 may be used to program or adjust operation of the medical device 302 and/or the sensor 304. The management device 306 may be any portable electronic, computing device including, for example, a dedicated controller, such as processor 361, a smartphone, or a tablet. In an example, the management device (PDM) 306 may include a processor 361, a management device management device memory 363, and a communication device 364. The management device 306 may contain analog and/or digital circuitry that may be implemented as a processor 361 (or controller) for executing processes to manage a user's blood glucose levels and for controlling the delivery of the drug or therapeutic agent to the user. The processor 361 may also be operable to execute programming code stored in the management device management device memory 363. For example, the management device management device memory 363 may be operable to store an artificial pancreas (AP) application 369 that may be executed by the processor 361. The processor 361 may when executing the artificial pancreas application 369 may be operable to perform various functions, such as those described with respect to the examples in FIGS. 1 and 2. The communication device 364 may be a receiver, a transmitter, or a transceiver that operates according to one or more radio-frequency protocols. For example, the communication device 364 may include a cellular transceiver and a Bluetooth transceiver that enables the management device 306 to communicate with a data network via the cellular transceiver and with the sensor 304 and the medical device 302. The respective transceivers of communication device 364 may be operable to transmit signals containing information useable by or generated by the AP application or the like. The communication devices 326, 346 and 376 of respective medical device 302, sensor 304 and smart accessory device 307 may also be operable to transmit signals containing information useable by or generated by the AP application or the like.

The medical device 302 may communicate with the sensor 304 over a wireless link 308 and may communicate with the management device 306 over a wireless link 331. The sensor 304 and the management device 306 may communicate over a wireless link 322. The smart accessory device 307, when present, may communicate with the medical device 302, the sensor 304 and the management device 306 over wireless links 391, 392 and 393, respectively. The wireless links 308, 331, 322, 391, 392 and 393 may be any type of wireless link operating using known wireless standards or proprietary standards. As an example, the wireless links 308, 331, 322, 391, 392 and 393 may provide communication links based on Bluetooth®, Wi-Fi, a near-field communication standard, a cellular standard, or any other wireless protocol via the respective communication devices 326, 346, 364 and 374. In some examples, the medical device 302, smart accessory device 307, and/or the management device 306 may include a user interface 327, 378 and 368, respectively, such as a keypad, a touchscreen display, levers, buttons, a microphone, a speaker, a display, or the like, that is operable to allow a user to enter information and allow the management device to output information for presentation to the user.

In various examples, the drug delivery system 300 may implement the artificial pancreas (AP) algorithm (and/or provide AP functionality) to govern or control automated delivery of insulin to a user (e.g., to maintain euglycemia—a normal level of glucose in the blood). The AP application may be implemented by the medical device 302 and/or the sensor 304. The AP application may be used to determine the times and dosages of insulin delivery. In various examples, the AP application may determine the times and dosages for delivery based on information known about the user, such as the user's sex, age, weight, or height, and/or on information gathered about a physical attribute or condition of the user (e.g., from the sensor 304). For example, the AP application may determine an appropriate delivery of insulin based on glucose level monitoring of the user through the sensor 304. The AP application may also allow the user to adjust insulin delivery. For example, the AP application may allow the user to issue (e.g., via an input) commands to the medical device 302, such as a command to deliver an insulin bolus. In some examples, different functions of the AP application may be distributed among two or more of the management device 306, the medical device (pump) 302 or the sensor 304. In other examples, the different functions of the AP application may be performed by one device, such the management device 306, the medical device (pump) 302 or the sensor 304.

As described herein, the drug delivery system 300 or any component thereof, such as the medical device may be considered to provide AP functionality or to implement an AP application. Accordingly, references to the AP application (e.g., functionality, operations, or capabilities thereof) are made for convenience and may refer to and/or include operations and/or functionalities of the drug delivery system 300 or any constituent component thereof (e.g., the medical device 302 and/or the management device 306). The drug delivery system 300—for example, as an insulin delivery system implementing an AP application—may be considered to be a drug delivery system or an AP application-based delivery system that uses sensor inputs (e.g., data collected by the sensor 304).

In an example, one or more of the devices, 302, 304, 306 or 307 may be operable to communicate via a wireless communication link 388 with cloud-based services 311. The cloud-based services 311 may utilize servers and data storage (not shown). The communication link 388 may be a cellular link, a Wi-Fi link, a Bluetooth link, or a combination thereof, that is established between the respective devices 302, 304, 306 or 307 of system 300. The data storage provided by the cloud-based services 311 may store anonymized data, such as user weight, blood glucose measurements, age, meal carbohydrate information, or the like. In addition, the cloud-based services 311 may process the anonymized data from multiple users to provide generalized information related to the various parameters used by the AP application. For example, an age-based general target blood glucose value may be derived from the anonymized data, which may be helpful when a user first begins using a system such as 300. The cloud-based services 311 may also provide processing services for the system 300, such as performing the process 100 in the example of FIG. 2 or additional processes, such as that described below with reference to FIG. 3.

In an example, the device 302 includes a communication device 364, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 311. For example, outputs from the sensor 304 or the medical device (pump) 302 may be transmitted to the cloud-based services 311 for storage or processing via the transceivers of communication device 364. Similarly, medical device 302, management device 306 and sensor 304 may be operable to communicate with the cloud-based services 311 via the communication link 388.

In an example, the respective receiver or transceiver of each respective device, 302, 306 or 307, may be operable to receive signals containing respective blood glucose measurement values of the number of blood glucose measurement values that may be transmitted by the sensor 304. The respective processor of each respective device 302, 306 or 307 may be operable to store each of the respective blood glucose measurement values in a respective memory, such as 323, 363 or 373. The respective blood glucose measurement values may be stored as data related to the artificial pancreas algorithm, such as 329, 349, 369 or 379. In a further example, the AP application operating on any of the management device 306, the smart accessory device 307, or sensor 304 may be operable to transmit, via a transceiver implemented by a respective communication device, 364, 374, 346, a control signal for receipt by a medical device. In the example, the control signal may indicate an amount of insulin to be expelled by the medical device 302.

Various operational scenarios and examples of processes performed by the system 300 are described herein. For example, the system 300 may be operable to implement the process examples of FIG. 1-4C.

The techniques described herein for providing functionality to determine when to softened upper bounds of insulin delivery and how much to soften the upper bound; predict future blood glucose measurement values by calculating deviations between predicted blood glucose measurement values and additional blood glucose measurement values; determining a gain parameter for use with a model of predicting a user's blood glucose measurement values and determining future insulin dosages; determine safety constraints based on an evaluation of missing blood glucose measurement values; determine safety constraints based on an evaluation of a user's increased interaction with an automatic insulin delivery device; and calculate a bolus uncertainty metric to determine an amount of insulin to be provided in a bolus dosage in response to a bolus request may be implemented using a number of different approaches. For example, the system 300 or any component thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. For example, the disclosed AP application and algorithms may be operable to perform various functions related to open loop operations, such as the generation of prompts identifying the softened upper bound that presented to a user via a user interface. Similarly, a dosage amount of insulin may be received by the AP application or algorithm from a user via a user interface. Other open-loop actions may also be implemented by adjusting user settings or the like in an AP application or algorithm.

Some examples of the disclosed device may be implemented, for example, using a storage medium, a computer-readable medium, or an article of manufacture which may store an instruction or a set of instructions that, if executed by a machine (i.e., processor or microcontroller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A system, comprising:

a processor;

a memory storing programming code, wherein the programming code is executable by the processor; and a transceiver operable to receive and transmit signals containing information usable by or generated by the processor, wherein the processor when executing the programming code is configured to:

receive a request to deliver a bolus;

determine a time of day a user requested a bolus for a plurality of prior requested boluses within a predetermined time period;

identify a number of bolus deliveries that occurred within a predetermined segment of time within the predetermined time period;

calculate a modified user bolus insulin dosage based on the identified number of bolus deliveries that occurred within the predetermined segment of time; and in response to a subsequent bolus request, forward an instruction to deliver a bolus according to the modified user bolus insulin dosage.

2. The system of claim 1, wherein the predetermined period of time is greater than 1 hour and the predetermined segment of time is less than the predetermined time period.

3. The system of claim 1, wherein the processor is further configured to:

calculate a bolus metric using times of prior boluses and a number of boluses; and evaluate the bolus uncertainty metric to determine when to deliver the bolus.

4. The system of claim 3, wherein the processor is further configured to:

revise the modified user bolus insulin dosage using the bolus metric.

5. The system of claim 1, further comprising:

a personal diabetes management device, including a processor and a user interface, wherein the personal diabetes management device configured to:

generate a signal indicating the request to deliver the bolus; and output the signal indicating the request to deliver the bolus for receipt by the transceiver, wherein the personal diabetes management device is communicatively coupled to the transceiver.

6. The system of claim 1, further comprises:

a wearable drug delivery device communicatively coupled to the processor, wherein the wearable drug delivery device includes a pump mechanism, wherein the wearable drug delivery device is operable to:

actuate the pump mechanism in response to the forwarded instruction to deliver the bolus according to the modified user bolus insulin dosage.

7. The system of claim 1, wherein the processor is configured to calculate the modified user bolus based on a bolus uncertainty metric comprising an indication of relative accuracy of a user's bolusing needs.

8. The system of claim 1, wherein the processor is configured to calculate the modified user bolus based on a bolus uncertainty metric, wherein the bolus uncertainty metric is based on an average number of bolus events.

9. The system of claim 1, wherein the processor is configured to calculate the modified user bolus based on a bolus uncertainty metric, wherein the bolus uncertainty metric is based on a bolus event and bolus events that occurred within the predetermined time period of the bolus event.

10. The system of claim 1, wherein the processor is further configured to:

evaluate a value of a bolus uncertainty metric with respect to a threshold; and in response to the evaluation, change the modified user bolus insulin dosage.

11. The system of claim 1, further comprising:

a user interface operable to receive the request to deliver the bolus.

12. The system of claim 11, wherein the user interface is located on a medical device.

13. A non-transitory, computer readable storage medium embodied with programming code that is configured, when executed by a processor, to cause the processor to:

receive a request to deliver a bolus;

determine a time of day a user requested a bolus for a plurality of prior requested boluses within a predetermined time period;

identify a number of bolus deliveries that occurred within a predetermined segment of time within the predetermined time period;

calculate a modified user bolus insulin dosage based on the identified number of bolus deliveries that occurred within the predetermined segment of time; and in response to a subsequent bolus request, forward an instruction to deliver a bolus according to the modified user bolus insulin dosage.

14. The non-transitory, computer readable storage medium of claim 13, wherein the instructions, when executed by the processor, cause the processor to calculated the modified user bolus based on a bolus metric.

15. The non-transitory, computer readable storage medium of claim 13, wherein the instructions, when executed by the processor, cause the processor to calculated the modified user bolus based on a bolus metric, wherein the bolus metric is based on an average number of bolus events that occurred within the predetermined time period of the bolus event.

16. The non-transitory, computer readable storage medium of claim 13, wherein the instructions, when executed by the processor, cause the processor to calculated the modified user bolus based on a bolus metric, wherein the bolus metric is based on a bolus event and bolus events that occurred within the predetermined time period of the bolus event.

17. The non-transitory, computer readable storage medium of claim 13, wherein the predetermined period of time is greater than 1 hour and the predetermined segment of time is less than the predetermined time period.

18. The non-transitory, computer readable storage medium of claim 13, wherein the programming code, when executed by the processor, cause the processor to:

calculate a bolus metric using times of prior boluses and a number of boluses; and evaluate the bolus metric to determine when to deliver the bolus.

19. The non-transitory, computer readable storage medium of claim 13, wherein the programming code, when executed by the processor, cause the processor to:

generate a signal to actuate a pump mechanism to deliver the bolus according to the modified user bolus insulin dosage.

20. The non-transitory, computer readable storage medium of claim 13, wherein the programming code, when executed by the processor, cause the processor to:

evaluate a value of a bolus metric with respect to a threshold; and in response to the evaluate, change the modified user bolus insulin dosage.

* * * * *